United States Patent [19]
Weidmann et al.

[11] Patent Number: 6,093,730
[45] Date of Patent: Jul. 25, 2000

[54] SUBSTITUTED ISOQUINOLINE-3-CARBOXAMIDES, THEIR PREPARATION AND THEIR USE AS PHARMACEUTICALS

[75] Inventors: Klaus Weidmann, Kronberg; Karl-Heinz Baringhaus, Wölfersheim; Georg Tschank, Essenheim; Ulrich Werner, Miehlen, all of Germany

[73] Assignee: Hoechst Marion Roussel Deutschland GmbH, Frankfurt Am Main, Germany

[21] Appl. No.: 09/174,558

[22] Filed: Oct. 19, 1998

[30] Foreign Application Priority Data

Oct. 20, 1997 [DE] Germany .......................... 197 46 287

[51] Int. Cl.[7] .......................... C07D 217/00; A61K 31/47
[52] U.S. Cl. .............................. 514/309; 546/141
[58] Field of Search .............. 546/141; 514/309

[56] References Cited

U.S. PATENT DOCUMENTS

| 5,204,338 | 4/1993 | Baader et al. | 514/183 |
| 5,428,046 | 6/1995 | Weidmann et al. | 514/355 |
| 5,607,954 | 3/1997 | Weidmann et al. | 514/355 |
| 5,620,995 | 4/1997 | Weidmann et al. | 514/356 |
| 5,658,933 | 8/1997 | Weidmann et al. | 514/350 |
| 5,719,164 | 2/1998 | Weidmann et al. | 514/312 |
| 5,726,305 | 3/1998 | Weidmann et al. | 546/156 |

FOREIGN PATENT DOCUMENTS

| 457 163 | 11/1991 | European Pat. Off. . |
| 0 548 883 | 6/1993 | European Pat. Off. . |
| 562 512 | 9/1993 | European Pat. Off. . |
| 590 520 | 4/1994 | European Pat. Off. . |
| 0 650 961 | 5/1995 | European Pat. Off. . |
| 661 269 | 7/1995 | European Pat. Off. . |
| 0 765 871 | 4/1997 | European Pat. Off. . |

OTHER PUBLICATIONS

Franklin et al, Chemical Abstract, vol. 115, No. 21, Abstract 222, 779, &, p. 21, Nov. 25, 1991.
Majamaa et al., "The 2-oxoglutarate Binding Site of Prolyl 4-Hydroxylase", Eur. J. Biochem, 138:239-245 (1984).
Cunliffe et al., "Novel Inhibitors of Prolyl 4-Hydroxylase. 3.[1] Inhibition by the Substrate Analogue N-Oxaloglycine and Its Derivatives", J. Med. Chem. 35:2652-2658 (1992).
Jollés et al., "Pristinamycine. Synthèse de L'heptapeptide Linéair et D'oligopeptides Correspondant au Constituant I$_A$ de la Pristinamycine", Bull. Soc. Chim, FR. 8:2252-2259 (1965).
English translation of Abstract of French article: Pristinamycine. Synthèse de L'heptapeptide Linéaire et D'oligopeptides Correspondant au Constituant 1$_A$ de la Pristinamycine, 1965.
Franklin et al., "Approaches to the Design of Anti-Fibrotic Drugs," Biochem. Soc. Trans., 19:812-815 (1991).
T.J. Franklin, "Therapeutic Approaches to Organ Fibrosis", Int. J. Biochem. Cell. Biol. 29(1):79-89 (1997).
Greene et al., "Protective Groups in Organic Synthesis", Chapters 2 and 3, pp. 10-174 (1991).
Suzuki et al., "A Facile Synthesis of 1-Oxo-1,2-dihydroisoquinoline-3-carboxylate and 2-Pyridone-6-carboxylate Derivatives", Synthesis 461-462 (1978).
Nunami et al., "Reaction of Phthalic Anhydrides with Methyl Isocyanoacetate: A Useful Synthesis of 1,2-Dihydro-1-oxoisoquinolines[1]", Chem. Pharm. Bull. 27(6):1373-1377 (1979).
Caswell et al., "A Study of the Hydroxy- and Methoxyphthalimidoacetic Acids and the Methyl Methoxy-phthalimidoacetates (1,2)" J. Heterocycl. Chem. 3:328-332 (1966).
Fowler et al., "Cyclic Imides. IX. Displacement of Halide From N-Substituted 3-Halophthalimides by Methoxide Ion (1.2)", 10:407-408 (1973).
Kivirikko et al., "Modifications to a Specific Assay for Hydroxyproline in Urine", Anal. Biochem. 19:249-255 (1967).
Kaule et al., "Assay for 2-Oxoglurate Decarboxylating Enzymes Based on the Determination of [1-$^{14}$c] Succinate: Application to Prolyl 4-Hydroxylase", Anal. Biochem. 184:291-297 (1990).
Ryoo et al., "Studies on Plasma Protein Synthesis With a New Liver Perfusion Apparatus", P.S.E.B.M., 128:760-772 (1968).
Tuderman et al., "An Affinity-Column Procedure Using Poly(L-proline) for the Purification of Prolyl Hydroxylase", Eur. J. Biochem., 52:9-16 (1975).

(List continued on next page.)

Primary Examiner—Zinna Northington Davis
Attorney, Agent, or Firm—Finnegan, Henderson, Farabow, Garrett & Dunner, L.L.P.

[57] ABSTRACT

Novel isoquinoline-3-carboxamides of the formula I:

(I)

[Structure: isoquinoline ring with substituents $R^1$, $R^2$, $R^3$, $R^4$, $R^5$, OH, and —NH—CH$_2$—CO$_2$H carboxamide group]

in which $R_1$ is hydrogen or chlorine, $R^2$ is hydrogen, alkyl, alkoxy, chlorine, trifluoromethyl, hydroxyl, or benzyloxy which is optionally substituted, or fluoroalkoxy of the formula O—[CH$_2$]$_x$—C$_f$H$_{(2f+1-g)}$F$_g$, where x=0 or 1, f=1-5, and g=1 to (2f+1), $R^3$ is hydrogen, alkyl, alkoxy, fluorine, chlorine, cyano, trifluoromethyl, hydroxyl, or benzyloxy which is optionally substituted, or fluoroalkoxy of the above formula, $R^4$ and $R^5$ are hydrogen, alkyl, fluorine, chlorine, bromine, trifluoromethyl, cyano, alkoxy, or fluoroalkoxy of the above formula, including the physiologically active salts, are strong prolyl-4-hydroxylase inhibitors which do not cause steatosis.

37 Claims, No Drawings

OTHER PUBLICATIONS

Kedersha et al., "An Improved Method for the Purification of Vertebrate Prolyl Hydroxylase by Affinity Chromatography", Collagen Rel. Res., 1:345–353 (1981).

M. Chojkier, "Hepatocyte Collagen Production In Vivo in Normal Rats,"J. Clin. Invest., 78:333–339, 1986.

Ogata et al., "Minor Contribution of Hepatocytes to Collagen Production in Normal and Early Fibrotic Rat Livers", Hepatology 14(2):361–367 (1991).

Blomhoff et al., "Isolation and Cultivation of Rat Liver Stellate Cells" Methods Enzymol., 90(6):58–71, 1990.

Chojkier et al., "A New Method for Determining the Extent of Proline Hydroxylation by Measuring the Ratio of [4–$^3$H]:[$^{14}$C]Proline in Collagenase Digests", Anal. Biochem., 108:385–393 (1980).

H. Schimassek, "Metabolite des Kohlenhydratstoffwechsels der Isoliert Perfundierten Rattenleber", H. Biochemin. Z. 336:460–467 (1963).

English translation of Abstract of German article: "Metabolite des Kohlenhydratsoffwechsels der Isoliert Perfundierten Rattenleber".

C. Rouiller, "Experimental Toxic Injury of the Liver", THE LIVER, vol. 2, pp. 335–476 (1964), New York, Academic Press, New York.

Caswell et al., "Cyclic Imides. VII. Carboxyphthalimidoacetic Acids (1.2)", J. Heterocycl. Chem. 865–867 (1968).

English Derwent Abstract of EP 0 650 961, 1995.

European Search Report dated May 20, 1999.

English Derwent Abstract of EP 0 548 883, 1993.

SUBSTITUTED ISOQUINOLINE-3-CARBOXAMIDES, THEIR PREPARATION AND THEIR USE AS PHARMACEUTICALS

This application claims the benefit of priority of German application 19746287.1, filed Oct. 20, 1997, and incorporates by reference that application.

The invention relates to substituted isoquinoline-3-carboxamides, their preparation, their use as inhibitors of prolyl-4-hydroxylase, and their use as pharmaceuticals for the treatment of fibrotic disorders.

Compounds which inhibit the enzyme prolyl hydroxylase cause a very selective inhibition of collagen biosynthesis by affecting the collagen-specific hydroxylation reactions. In the course of these, protein-bound proline or lysine is hydroxylated by the enzyme prolyl or lysyl hydroxylase. If this reaction is suppressed by inhibitors, a nonfunctional, underhydroxylated collagen molecule results, which can be released into the extracellular space by the cells only in a small amount. The underhydroxylated collagen additionally cannot be incorporated into the collagen matrix and is very easily proteolytically degraded. As a result of these effects, the amount of extracellularly deposited collagen is decreased overall.

Inhibitors of prolyl hydroxylase are therefore suitable substances in the therapy of disorders in which the deposition of collagens decisively contributes to the clinical picture. These include, inter alia, fibroses of the lung, liver and skin (scleroderma and scarring after burns, injuries and surgical interventions) and also atherosclerosis.

It is known that the enzyme prolyl hydroxylase is effectively inhibited by pyridine-2,4- and pyridine-2,5-dicarboxylic acid (Majamaa et al., EUR. J. BIOCHEM. 138 (1984) 239–45). In cell culture, however, these compounds are only active as inhibitors in very high concentrations (Tschank et al., BIOCHEM. J. 238 (1987) 625–33).

Prodrugs of pyridine-2,4(5)-dicarboxylates are also known. These are described in EP-A-0 590 520 and EP-A-0 562 512.

N-Oxalylglycine as inhibitors of prolyl4-hydroxylase are known from Cunliffe et al., J. MED. CHEM. 35 (1992) 2652–58, and EP-A-0 457 163.

3-Hydroxypyridine-2-carboxylic acid N-(carboxymethyl)amide is known from Yoiles et al., BULL. SOC. CHIM. FR. 8 (1965) 2252–59.

N-((4-Hydroxyisoquinolin-3-yl)carbonyl)glycine and N-((7-bromo-4-hydroxy-isoquinolin-3-yl)carbonyl)glycine are known from Franklin et al., BIOCHEM. SOC. TRANS. 19 (1991) 812–15, the in-vivo activity on collagen biosynthesis being poor in the case of N-((4-hydroxyisoquinolin-3-yl)carbonyl)glycine. Hydroxyquinolinecarboxylic acid glycylamides are also mentioned here. In Franklin, "Therapeutic Approaches to Organ Fibrosis", INT. J. BIOCHEM. CELL. BIOL. 29(1) (1997) 79–89, a toxic action on the liver (steatosis) in rats is reported in the case of N-((7-bromo-4-hydroxyisoquinolin-3-yl)carbonyl)glycine in addition to the in-vivo inhibition of collagen biosynthesis.

EP-A-0 661 269 describes substituted heterocyclic carboxamides and their use as inhibitors of prolyl-4-hydroxylase and as inhibitors of collagen biosynthesis.

The object of the present invention was to search for more highly active inhibitors of prolyl hydroxylase. The object was furthermore to search for active inhibitors of prolyl hydroxylase which do not cause steatosis. It has now been found that novel isoquinoline-3-carboxamides are surprisingly strong prolyl-4-hydroxylase inhibitors which do not cause steatosis.

The compounds according to the invention correspond to the formula I:

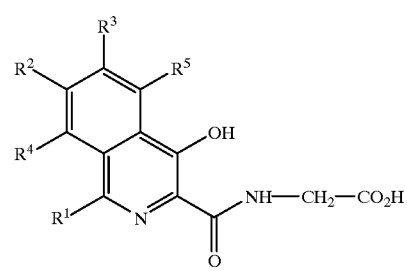

in which
$R^1$ is hydrogen or chlorine;
$R^2$ is hydrogen, $(C_1-C_8)$-alkyl, $(C_1-C_8)$-alkoxy, chlorine, trifluoromethyl, hydroxyl, benzyloxy, which is unsubstituted or substituted by a substituent selected from the group consisting of $(C_1-C_5)$-alkyl and $(C_1-C_5)$-alkoxy, or fluoroalkoxy of the formula

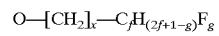

where
x=0 or 1,
f=an integer from 1 to 5, and
g=an integer from 1 to (2f+1);
$R^3$ is hydrogen, $(C_1-C_8)$-alkyl, $(C_1-C_8)$-alkoxy, fluorine, chlorine, cyano, trifluoromethyl, hydroxyl, benzyloxy which is unsubstituted or substituted by a substituent selected from the group consisting of $(C_1-C_5)$-alkyl and $(C_1-C_5)$-alkoxy, or fluoroalkoxy of the formula

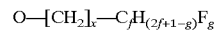

in which x, f, and g are as defined above; and
$R^4$ and $R^5$ independently are hydrogen, $(C_1-C_5)$-alkyl, fluorine, chlorine, bromine, trifluoromethyl, cyano, $(C_1-C_5)$-alkoxy, or fluoroalkoxy of the formula

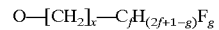

in which x, f, and g are as defined above,
or a physiologically active salt thereof.

Preferred compounds of the formula I are those in which
$R^1$ is hydrogen or chlorine;
$R^2$ is hydrogen, $(C_1-C_8)$-alkyl, $(C_1-C_8)$-alkoxy, chlorine, trifluoromethyl, hydroxyl, benzyloxy, or fluoroalkoxy of the formula

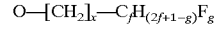

where
x=0 or 1,
f=an integer from 1 to 5, and
g=an integer from 1 to (2f+1);
$R^3$ is hydrogen, $(C_1-C_8)$-alkyl, $(C_1-C_8)$-alkoxy, fluorine, chlorine, cyano, trifluoromethyl, hydroxyl, benzyloxy, or fluoroalkoxy of the formula

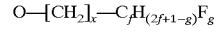

in which x, f, and g are as defined above;

R⁴ is hydrogen, $(C_1-C_8)$-alkoxy, fluorine, chlorine, trifluoromethyl, cyano, or fluoroalkoxy of the formula

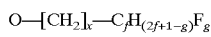

in which x, f, and g are as defined above; and
R⁵ is hydrogen.

Additionally preferred compounds of the formula I are those in which
R¹ is hydrogen or chlorine;
R² is hydrogen, $(C_1-C_5)$-alkoxy, chlorine, benzyloxy, fluoroalkoxy where x=0 and f=1;
R³ is hydrogen, $(C_1-C_5)$-alkoxy, chlorine, or benzyloxy;
R⁴ is hydrogen, chlorine, or methoxy; and
R⁵ is hydrogen.

Further preferred compounds are those in which
R¹ is hydrogen or chlorine;
R² is hydrogen, $(C_1-C_8)$-alkoxy, chlorine, hydroxyl, or benzyloxy;
R³ is hydrogen, $(C_1-C_8)$-alkoxy, fluorine, chlorine, hydroxyl, or benzyloxy;
R⁴ is hydrogen or chlorine; and
R⁵ is hydrogen.

Particularly preferred compounds of the formula I are those in which
R¹ is hydrogen or chlorine;
R² is $(C_1-C_8)$-alkoxy, chlorine, or benzyloxy; and
R³, R⁴, and R⁵ are hydrogen;
or in which
R¹ is hydrogen or chlorine;
R² is hydrogen or chlorine;
R³ is $(C_1-C_8)$-alkoxy, chlorine, or benzyloxy; and
R⁴ and R⁵ are hydrogen;
or in which
R¹ is hydrogen or chlorine;
R² and R³ independently are hydrogen or chlorine;
R⁴ is $(C_1-C_6)$-alkoxy, chlorine, or benzyloxy; and
R⁵ is hydrogen.

Additionally, particularly preferred compounds of the formula I are those in which
R¹ is hydrogen or chlorine;
R² is $(C_1-C_6)$-alkoxy or benzyloxy;
R³, R⁴, and R⁵ are hydrogen;
or in which
R¹ is hydrogen or chlorine;
R² is hydrogen;
R³ is $(C_1-C_6)$-alkoxy or benzyloxy; and
R⁴ and R⁵ are hydrogen.

Especially preferred compounds of the formula I are those in which
R¹ is hydrogen or chlorine,
R² is $(C_1-C_6)$-alkoxy, and
R³, R⁴, and R⁵ are hydrogen;
or in which
R¹ is hydrogen or chlorine;
R² is hydrogen;
R³ is $(C_1-C_6)$-alkoxy; and
R⁴ and R⁵ are hydrogen.

Very particular mention may be made of the following compounds:

N-((1-chloro-4-hydroxyisoquinolin-3-yl)carbonyl) glycine;
N-((8-chloro-4-hydroxyisoquinolin-3-yl)carbonyl) glycine;
N-((1-chloro4-hydroxy-7-(2-propyloxy)isoquinolin-3-yl) carbonyl)glycine; and
N-((4-hydroxy-7-(2-propyloxy)isoquinolin-3-yl) carbonyl)glycine.

In addition, the object of the present invention was to search for active inhibitors of prolyl hydroxylase which are liver-selective.

It has now been found that novel isoquinoline-3-carboxylic acid N-(2-hydroxyethyl)amides of the formula Ia are alcohol prodrugs of the corresponding compounds of the formula I.

The prodrug compounds of the formula Ia according to the invention are oxidized to compounds of the formula I in the living body (in vivo) and in the isolated organ (perfused liver, in vitro). The conversion of the compounds of the formula I preferably takes place in the liver, as a result of which a liver-selective inhibition of prolyl-4-hydroxylase and of collagen biosynthesis is achieved.

After the administration of the compounds of the formula Ia, they cause an inhibition of prolyl-4-hydroxylase which is to be observed in vivo and in vitro, the compounds of the formula I being formed. These compounds inhibit prolyl4-hydroxylase and therefore lead to an inhibition of collagen biosynthesis.

The compounds according to the invention correspond to the formula Ia:

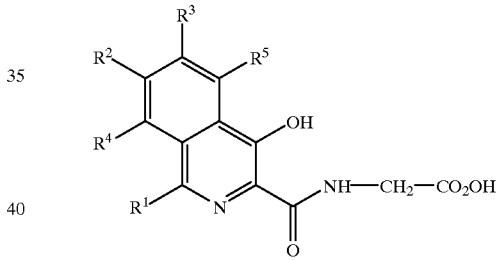

(Ia)

in which
R¹ is hydrogen or chlorine;
R² is hydrogen, $(C_1-C_8)$-alkyl, $(C_1-C_8)$-alkoxy, chlorine, trifluoromethyl, hydroxyl, benzyloxy, which is unsubstituted or substituted by a substituent selected from the group consisting of $(C_1-C_5)$-alkyl, and $(C_1-C_5)$-alkoxy, or fluoroalkoxy of the formula

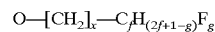

where
x=0 or 1,
f=an integer from 1 to 5, and
g=an integer from 1 to (2f+1);
R³ is hydrogen, $(C_1-C_8)$-alkyl, $(C_1-C_8)$-alkoxy, fluorine, chlorine, cyano, trifluoromethyl, hydroxyl, benzyloxy which is unsubstituted or substituted by a substituent selected from the group consisting of $(C_1-C_5)$-alkyl and $(C_1-C_5)$-alkoxy, or fluoroalkoxy of the formula

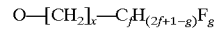

in which x, f, and g are as defined above; and $R^4$ and $R^5$ independently are hydrogen, $(C_1-C_5)$-Alkyl, fluorine, chlorine, bromine, trifluoromethyl, cyano, $(C_1-C_5)$-alkoxy, or fluoroalkoxy of the formula $$O-[CH_2]_x-C_fH_{(2f+1-g)}F_g$$

in which x, f, and g are as defined above,
or a physiologically active salt thereof.

Preferred compounds of the formula Ia are those in which
$R^1$ is chlorine;
$R^2$ and $R^3$ independently are hydrogen or $(C_1-C_4)$-alkoxy; and
$R^4$ and $R^5$ are hydrogen.

Particularly preferred compounds of the formula Ia are those in which
$R^1$ is hydrogen or chlorine;
$R^2$ is $(C_1-C_6)$-alkoxy; and
$R^3$, $R^4$ and $R^5$ are hydrogen;
or in which
$R^1$ is hydrogen or chlorine;
$R^2$ is hydrogen;
$R^3$ is $(C_1-C_6)$-alkoxy; and
$R^4$ and $R^5$ are hydrogen.

Very particular mention is made of the compound: 1-chloro-4-hydroxy-7-(2-propyloxy)isoquinoline-3-carboxylic acid N-(2-hydroxyethyl)amide.

As mentioned above, the invention furthermore comprises salts of the compounds of the formulae I and Ia. Salt formation with basic reagents can take place once or twice on the acidic groups of the compounds of the formulae I and Ia, i.e., on the radicals $R^1$, $R^2$, $R^3$, $R^4$, and $R^5$ and/or on the acidic phenolic OH group, in particular on the phenolic OH group.

Reagents used are, for example, alkoxides; hydroxides; carbonates; hydrogencarbonates; hydrogenphosphates; and/or metal organyls of the alkali metal and alkaline earth metal elements, of the elements of the 3th and 4th main group of the Periodic Table and of the transition metal elements;

amines, optionally substituted 1- to 3-times by $(C_1-C_8)$-hydroxyalkyl, $(C_1-C_4)$-alkoxy-$(C_1-C_8)$-alkyl, phenyl, benzyl or $(C_1-C_8)$-alkyl, which can be substituted 1- to 3-times by hydroxyl or $(C_1-C_4)$-alkoxy, for example tromethane (tris buffer), 2-aminoethanol, 3-aminopropanol, hydroxylamine, dimethylhydroxylamine, 2-methoxyethylamine, and 3-ethoxypropylamine;

basic amino acids and amino derivatives, such as amino acid esters, histidine, arginine and lysine and their derivatives; and pharmaceuticals which contain a basic group, such as, for example, amiloride, verapamil, and beta-blockers.

The invention furthermore includes prodrugs to the compounds of the formula (I), which cause an inhibition of collagen biosynthesis in vivo by release of compounds of the formula I or their salts.

Finally, the invention also includes prodrugs which cause an inhibitory action on prolyl-4-hydroxylase in vivo by release of compounds of the formula I or their salts.

Prodrug groups are chemical groups which in vivo
are converted to the carboxylate group of the compounds of the compound I and/or,
can be removed from the amide N atom, and/or,
can be converted to a quinoline ring.

The suitable prodrug groups are known to the person skilled in the art.

In particular, mention may be made of the following prodrug groups: for the carboxylate group ester, amide, hydroxymethyl, and aldehyde groups and their derivatives, for the quinoline N atom N-oxides and N-alkyl derivatives.

The invention relates to the use of compounds of the formula I and the physiologically tolerable salts for the inhibition of collagen biosynthesis.

The invention relates to the use of compounds of the formula I and the physiologically tolerable salts for the inhibition of prolyl-4-hydroxylase.

The invention furthermore relates to the use of compounds of the formula I and the physiologically tolerable salts for the production of a pharmaceutical against fibrotic disorders.

The invention furthermore relates to the use of compounds of the formula I and the physiologically tolerable salts for the production of a pharmaceutical against fibrotic disorders of the liver, the kidney, the lung and the skin.

The invention finally relates to the compounds of the formula I for use as pharmaceuticals.

The invention in particular relates to the compounds of the formula I for use as fibrosuppressants.

The invention additionally relates to the use of compounds of the formula Ia and the physiologically tolerable salts for the production of a pharmaceutical against fibrotic disorders of the liver.

Compounds of the formulae I and Ia with 4-mercapto are likewise effective inhibitors of prolyl-4-hydroxylase. The corresponding 3-mercaptopyridine-2-carboxamides are disclosed in EP-A 0 661 269.

The invention furthermore relates to a process for the preparation of compounds of the formula I. The compounds of the formula I may be prepared by:

1.I) reacting quinoline-2-carboxylic acids of the formula II with the amino esters of the formula III to give the amide esters of the formula IV; and 1.ii) releasing the compounds of the formula I from their esters of the formula

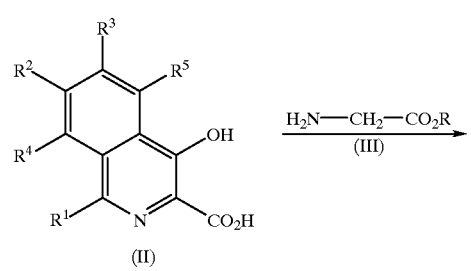

-continued

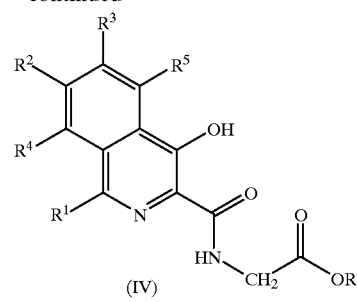

(IV)

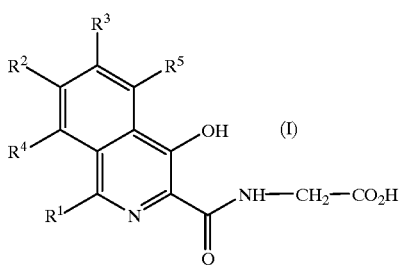

(I)

in which R is H, $(C_1-C_8)$-alkyl, or benzyl.

The 4-hydroxyl group of the compound of the formula II can also be present here in protected form. Suitable protective groups ("PG"), such as are familiar to the person skilled in the art, are, in particular, benzyl, p-methoxybenzyl, 3,4-dimethoxybenzyl, alkyl, methoxymethyl ("MOM"), methylthio, benzyloxymethyl ("BOM"), t-butyloxymethyl, 2-methoxyethoxymethyl ("MEM") and tetrahydropyranyl ("THP"). Further protective groups and the conditions for their removal (conversion of compounds of the formula V into compounds of the formula I) are described by Greene et al., "Protective Groups in Organic Synthesis", Chapters 2 and 3, pp. 10–174 (1991).

Suitable processes for the amide formation (reaction 1.I) are the methods of carboxyl activation and the condensation reactions known from peptide chemistry. Reagents which can be used for carboxylic acid activation are the substances known to the person skilled in the art, such as thionyl chloride, oxalyl chloride, pivaloyl chloride, chloroformic acid ester derivatives, or N,N'-carbonyidimidazole. The activated derivatives of the compounds of the formula II are reacted with the amide derivatives of the formula III after preparation in situ.

A suitable condensing agent is, for example, the combination of N,N'-dicyclohexylcarbodiimide, 1-hydroxy-1H-benzotriazole, (benzotriazol-1-yloxy) tripyrrolidinophosphonium hexafluorophosphate ("PyBOP") and N-ethylmorpholine.

Suitable solvents are dichloromethane, tetrachloromethane, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane, and/or pyridine.

Substituted 4-hydroxyisoquinoline-3-carboxylic acids and their esters of the formula III (IIa and IIb) are obtainable from corresponding 4-hydroxy-1(2H)-isoquinolone-3-carboxylic acid esters of the formula V:

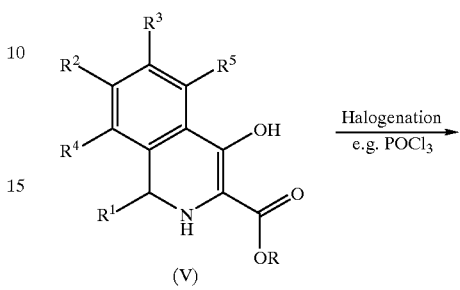

(V)

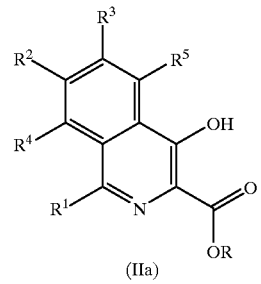

(IIa)

Reduction
H$_2$/Pd catalyst

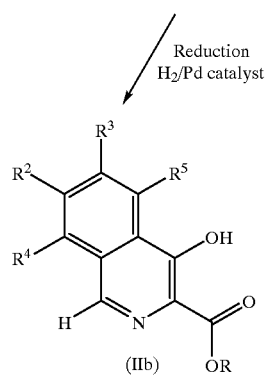

(IIb)

in which R is H$_1$ $(C_1-C_8)$-alkyl, or benzyl.

The substituted 4-hydroxy-1(2H)-isoquinolone-3-carboxylic acid esters of the formula V can be prepared by the following methods:

1. By reaction of phthalic anhydrides with isocyanoacetic acid esters/DBU and the acidic isomerization of the isolated 1,3-oxazoles, as described in Suzuki et al., SYNTHESIS 461 (1978) and Nunami et al., CHEM. PHARM BULL. 27 (1979) 1373, or 2. By the alkoxide-catalyzed rearrangement of phthalimidoacetates of the formula VI to hydroxyisoquinolone esters (Gabriel-Colman rearrangement), as is described, for example in Caswell and Atkinson, J. HETEROCYCL. CHEM. 328 (1966);

J. HETEROCYCL. CHEM. 865 (1968); and J. HETEROCYCL. CHEM. 407 (1973):

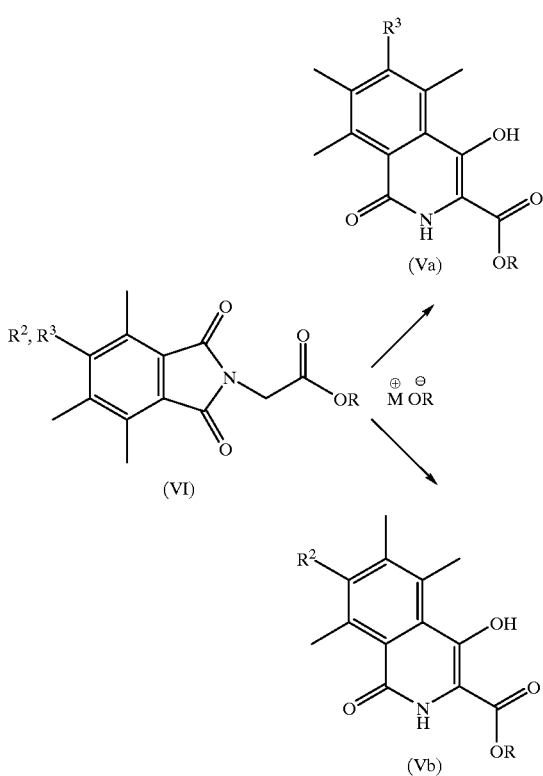

in which R is H, $(C_1-C_8)$-alkyl, or benzyl.

For the preparation of the compounds of the formula Ia the compounds of the formula IIa or IIb are reacted with 2-aminoethanol.

The compounds of the formulae I and Ia are inhibitors of prolyl4-hydroxylase. The inhibition of this enzyme was determined as described by Kaule and Günzler, ANAL. BIOCHEM. 184 (1990) 291–97.

The compounds of the formulae I and Ia according to the invention furthermore have valuable pharmacological properties and exhibit, in particular, antifibrotic activity, as shown in Table I below:

TABLE I

| Example No. | IC$_{50}$ [µmol] |
|---|---|
| 1 | 0.12 |
| 2 | 1.90 |
| 3 | 0.79 |
| 4 | 0.57 |
| 5 | 0.70 |
| 6 | 2.02 |
| 7 | 1.34 |
| 8 | 0.62 |
| 9 | 2.30 |
| 10 | 3.60 |
| 11 | 0.66 |
| 12 | 0.65 |
| 13 | 9.30 |
| 14 | 0.35 |
| 15 | 0.66 |

The antifibrotic action was determined in the model of carbon tetrachloride-induced liver fibrosis. For this, rats were treated twice weekly with CCl$_4$ (1 ml/kg) dissolved in olive oil. The test substance was administered daily, if appropriate even twice daily, orally or intraperitoneally dissolved in a suitable compatible solvent. The extent of the liver fibrosis was determined histologically and the proportion of collagen in the liver was analyzed by hydroxyproline determination as described in Kivirikko et al., ANAL. BIOCHEM. 19 (1967) 249 f. The fibrogenesis activity was determined by radioimmunological determination of collagen fragments and procollagen peptides in the serum. The compounds according to the invention were active in this model in a concentration of 1 to 100 mg/kg.

Control Animals:

In direct comparison to untreated animals, the hydroxyproline content of the liver increased by 200% after four weeks (administration twice per week) as a result of treatment with carbon tetrachloride. The measurement of the inhibition of hydroxyproline formation by the test substances was based on this level.

Substance Administration:

Here the experimental animals were treated for two weeks only with carbon tetrachloride, then for the next two weeks with carbon tetrachloride and test substance. The test substances were administered intraperitoneally twice per day in the total amount indicated below in Table II, Results:

TABLE II

| Test substance from Example | Dose [mg/kg] (number of animals) | Inhibition of hydroxyproline formation |
|---|---|---|
| 1 | 20 (15) | −55% |
| 9 | 20 (15) | −67% |
|  | 40 (15) | −65% |
|  | 100 (24) | −58% |
|  | 100* (14) | −71% |
| 19 | 40 (13) | −39% |

*oral administration

The fibrinogenesis activity was determined by radioimmunological determination of the N-terminal propeptide of collagen type III or of the—or C-terminal crosslinking domains of collagen type IV (7s collagen or type IV collagen NC$_1$) in the serum.

For this purpose, the hydroxyproline, procollagen III peptide, 7s-collagen, and type IV collagen NC concentrations in the liver of a) untreated rats (control), b) rats to which carbon tetrachloride was administered (CCl$_4$ control), and c) rats to which first CCl$_4$ and then a compound according to the invention was administered, were measured (this test method is described by C. Rouiller, "Experimental Toxic Injury of the Liver", *The Liver, Vol. 2*, pp. 335–476 (1964), New York, Academic Press.)

Activity of the compounds according to the invention can furthermore be demonstrated in the following systems.

Inhibitory Action of the Prolyl4-hydroxylase Inhibitors in the Combined Liver Perfusion/enzyme Assay:

Liver tissue selectively converts inactive proinhibitors into active prolyl-4-hydroxylase inhibitors whose action is mainly displayed in this organ. In order to investigate the inhibitory action of such active proinhibitors, the compounds were employed in perfusion experiments on isolated rat liver. The inhibitory action was then measured in a prolyl-4-hydroxylase assay.

Method:

Unfasted male Wistar rats of 200–300 g body weight (Hoe:WISKf(SPF71)) were anesthetized with pentobarbital (5 mg/100 g of body weight i.p.). After cannulation of the portal vein, the liver was washed with 100 ml of heparinized saline solution (5 lU/ml) of 37° C. for 3 min. The fluid left the liver by the incised vena cava. The organ was then removed, attached to the perfusion apparatus and perfused at a flow rate of 30 ml/min with 100 ml of medium for 2 hours under recirculating conditions. Krebs-Ringer buffer containing bovine erythrocytes was used for the perfusion. For this, bovine blood was mixed 1:1 with a citrate solution in the slaughterhouse immediately after removal. This mixture was centrifuged at 6000 rpm for 10 min and the supernatant was removed. This process was repeated once using saline solution and twice using Krebs-Ringer buffer. The final perfusion solution contained 33.3% of the erythrocyte sediment and 66.7% of Krebs-Ringer buffer (Schimassek, H. BIOCHEM. Z. 336 (1963) 460–467).

Composition of the solutions used:

citrate solution:

| | |
|---|---|
| glucose monohydrate | 22.6 g |
| trisodium citrate | 4.0 g |
| citric acid | 5.5 g |
| NaCl | 4.2 g |
| to 1000 ml with distilled water | |
| Krebs-Ringer buffer: | |
| NaCl | 8.0 g |
| KCl | 0.2 g |
| NaHCO$_3$ | 1.0 g |
| NaH$_2$PO$_4$.H$_2$O | 0.1 g |
| CaCl$_2$ | 0.2 g |
| MgCl$_2$.6 H$_2$O | 0.1 g |
| Bovine serum albumin | 16 g |
| to 898 ml with distilled water, pH 7.4 | |

Perfusion apparatus (Ryoo and Tarver, H.P.S.E.B.M. 128 (1968) 760–72): The central element of the apparatus is a thermostated cylinder having a removable plate for the storage of the organ. The outlet tube is extended and its lower end is attached to a peristaltic pump. Before the return of the perfusate into the organ bath, it is passed through a glass spiral, which serves as a heat exchanger, which keeps the temperature constant at 37° C. At the bottom of the cylinder, the perfusate is aerated with 70 ml of a $CO_2/O_2$ mixture (5:95%) per minute. In order to avoid foam formation, 14 µl of 0.1% strength Genapol® PF-10 solution are added per ml of perfusion solution. Samples for analysis are removed from the perfusate at a position before entry into the perfused organ.

Treatment:

The test substances were added to the perfusion solution at time t=0 and 60 min in concentrations of 100 or 50 µg/ml in each case. After a perfusion time of 120 min, a sample of the perfusion solution was removed for analysis.

Enzyme Assay:

The inhibitory activity of the metabolites which are formed in the liver during the two-hour perfusion was determined in an in vitro prolyl-4-hydroxylase assay. The enzyme is purified from 14 day-old chicken embryos as described in the literature (Tuderman et al., EUR.J.BIOCHEM. 52 (1975) 9–16; Kedersha and Berg, COLLAGEN REL. RES. 1 (1981) 345–53). The enzyme test is carried out according to Kaule and Günzler, ANAL. BIOCHEM. 184 (1990) 291–97). Dose-response curves were obtained by means of dilution series, starting from the undiluted perfusion solution.

TABLE III

| | Inhibition of prolyl-4-hydroxylase, IC$_{50}$ (µM) Comparison substance from | |
|---|---|---|
| Example No. | Example No. | After perfusion |
| 19 | 1 | 10.5 |
| 20 | 2 | 16.6 |
| 21 | 3 | 7.5 |
| 22 | 4 | 6.4 |
| 23 | 5 | 21.7 |

Inhibition of Hepatic Prolyl-4-hydroxylase in Vivo:

This model is used for the demonstration of acute inhibition of prolyl-4-hydroxylase in vivo. For this, the test substance or the corresponding vehicle is administered (intraperitoneally, intravenously or orally) to rats of both sexes (healthy or with induced liver fibrosis) and $^{14}$C-L-proline (250 µCi/kg of body weight) is administered intraperitoneally after substance administration. An intraperitoneal administration of $^{14}$C-L-proline (250 µCi/kg of body weight) then takes place again. Finally, the animals are exsanguinated under pentobarbital anesthesia and the livers are removed. The purification of the hepatic collagen by pepsin degradation and fractional ammonium sulfate precipitation was carried out according to published protocols (Ref. 1, 2, supra). The purified liver collagen was hydrolyzed and the content of $^{14}$C-hydroxyproline and $^{14}$C-proline was determined by amino acid analysis by means of ion-exchange chromatography. An inhibition of prolyl-4-hydroxylase is clear from a lowering of the quotient $^{14}$C-hydroxyproline/[$^{14}$C-hydroxyproline+$^{14}$C-proline]. The reference substance used is 2,2'-dipyridyl. (Ref. 1: M. Chojkier, "Hepatocyte Collagen Production in vivo in Normal Rats", J. CLIN. INVEST. 78 (1986) 333–39 and Ref. 2: Ogata et al., "Minor Contribution of Hepatocytes to Collagen Production in Normal and Early Fibrotic Livers", HEPATOLOGY 14 (1991) 361–67.)

Inhibition of Prolyl-4-hydroxylase in Cell Cultures:

The following cell types are used for the testing of prolyl-4-hydroxylase inhibitors in cell cultures: Normal human dermal fibroblasts (NHDF) and primary fat-storing cells from the rat's liver (Ref. 3, supra). For this, the cells are cultured in the presence of inhibitors. At the same time, the collagen synthesized de novo in this time is metabolically labeled by 4-$^3$H-L-proline and $^{14}$C-proline. The effect of the test substances on the degree of hydroxylation of the collagen is then determined according to the method of Chojkier et al. (Ref. 4, supra). The reference substance employed is 2,2'-dipyridyl. (Ref. 3: Blomhoff and Berg, "Isolation and Cultivation of Rat Liver Stellate Cells", METHODS ENZYMOL. 190 (1990) 59–71, and Ref. 4: Chojkier et al., "A new Method for Determining the Extent of Proline Hydroxylation by Measuring Changes in the Ratio of [4-$^3$H]:[$^{14}$C] Proline in Collagenase Digests", ANAL. BIOCHEM. 108 (1980) 385–93.

It was not possible to demonstrate any liver steatosis in the treatment for up to six weeks of male rats (Fischer F344, Sprague Dawley, Wistar) with the compound of Example 9 (N-((1-chloro-4-hydroxyisoquinolin-3-yl)carbonyl)glycine, dissolved in water/NaHCO$_3$, administration of 2×25 mg/kg i.p/day).

The compounds of the formulae I and Ia can be used as medicaments in the form of pharmaceutical preparations which contain them, if appropriate with tolerable pharmaceutical excipients. The compounds can be used as therapeutics, e.g., in the form of pharmaceutical preparations which contain these compounds as a mixture with a pharmaceutical, organic or inorganic excipient suitable for enteral, percutaneous or parenteral administration, such as, for example, water, gum arabic, gelatin, lactose, starch, magnesium stearate, talc, vegetable oils, polyalkylene glycols, petroleum jelly etc.

For this purpose, they can be used orally in doses of 0.1 to 25 mg/kg/day, preferably 1 to 5.0 mg/kg/day, or parenterally in doses of 0.01 to 5 mg/kg/day, preferably 0.01 to 2.5 mg/kg/day, in particular 0.5 to 1.0 mg/kg/day. In severe cases, the dose can also be increased. In many cases, however, lower doses also suffice. These details relate to an adult of weight approximately 75 kg.

In the examples described below, the compounds of the formula I according to the invention are designated as substituted N-((isoquinolin-3-yl)carbonyl)glycines. Designation as substituted isoquinoline-3-carboxylic acid N-(carboxymethyl)amides (isoquinoline-3-carboxylic acid glycinamides) is also possible.

EXAMPLES OF THE PRESENT INVENTION

Example 1

N-((1-Chloro-4-hydroxy-7-(2-propyloxy) isoquinolin-3-yl)carbonyl)glycine a) Diethyl 4-(2-propyloxy)phthalate 54 g of 4-hydroxyphthalic acid were esterified under reflux for 4 h in 1.2 l of ethanol and 25 ml of conc. sulfuric acid. 60 g (0.252 mol) of diethyl ester were obtained, which was then stirred at 80° C. for 30 min with 37.3 g (0.27 mol) of powdered potassium carbonate in 250 ml of N,N-dimethylacetamide. 25.7 ml (0.26 mol) of 2-propyl iodide were added dropwise at 40° C. and the mixture was stirred at 100° C. for 90 min. After cooling, it was concentrated in vacuo, the residue was brought to pH 7 in water using 2N hydrochloric acid and the mixture was extracted twice with ethyl acetate. After drying over magnesium sulfate and concentrating, 65 g of an oily crude product were obtained.

b) 4-(2-Propyloxy)phthalic acid 65 g of the above diester were introduced into 400 ml of 3N ethanolic KOH at 20° C. and the mixture was stirred at 45° C. for 1 h. The precipitated K salt was filtered off with suction and dissolved in water, and the solution was brought to pH 1 while cooling with conc. aqueous hydrochloric acid and extracted twice with ethyl acetate. After drying and concentration of the organic phase, 44 g of the title compound were obtained; m.p. 116–118° C.

c) 4-((2-Propyloxy)phthaloyl)iminoacetic acid 44 g (0.2 mol) of the above dicarboxylic acid were stirred in an open flask at a bath temperature of 200° C. for 1 h with 16 g (0.2 mol) of glycine in 250 ml of Dowtherm. After cooling, the mixture was treated with 800 ml of petroleum ether, precipitated resin was taken up in 400 ml of saturated sodium bicarbonate solution, the mixture was extracted twice with ethyl acetate, the aqueous phase was brought to pH 1 using 2N aqueous hydrochloric acid and extracted twice with dichloromethane, and the organic phase was dried and concentrated. 47 g of product were obtained; m.p. 120–122° C.

d) 1-Butyl 4-((2-propyloxy)phthaloyl)iminoacetate 47 g of the above product were stirred at reflux for 1 h with 9 ml of conc. sulfuric acid in 600 ml of 1-butanol. After cooling, the mixture was concentrated in vacuo. The residue was dissolved in 300 ml of ethyl acetate, this solution was shaken with aqueous sodium bicarbonate solution, the organic phase was dried and concentrated, and the residue (54 g) was chromatographed on silica gel using ethyl acetate (n-heptane (1:5)). 42.4 g of product were obtained; m.p. 83–85° C.

e) 1-Butyl 4-hydroxy-7-(2-propyloxy)-1(2H)-isoquinolone-3-carboxylate (A) and 1-butyl 4-hydroxy-6-(2-propyloxy)-1(2H)isoquinolone-3-carboxylate (B)

3.2 g (140 mmol) of sodium were dissolved in 350 ml of 1-butanol under a nitrogen atmosphere with stirring at 60–80° C. 22.3 g (70 mmol) of the above compound were then added at 20° C. and the mixture was stirred at 95° C. for 45 min. The reaction solution turned from colorless to black, then to green. After cooling, the solution was stirred into 300 ml of 2N hydrochloric acid, the solid was filtered off with suction and the residue was treated with 150 ml of diethyl ether 11.5 g of product (B) were obtained, m.p. 168–170° C. 1.2 g of product A were obtained from the mother liquor. The butanol phase was dried and concentrated in vacuo, and the residue obtained was crystallized using diethyl ether. 5.2 g of product A were obtained; m.p. 118–123° C.

Differentiation of the isomers A and B also takes place on TLC with ethyl acetate on silica gel: A: $R_f$ about 0.5; B: $R_f$ about 0.35.

f) 1-Butyl 1-chloro-4-hydroxy-7-(2-propyloxy) isoquinoline-3-carboxylate 12 g of the above compound were heated to boiling for 30 min in 120 ml of phosphorus oxychloride. After working up and chromatography using ethyl acetate/heptane (1:5) on silica gel: 7.3 g of product; m.p. 60–62° C.

g) 1-Chloro-4-hydroxy-7-(2-propyloxy)isoquinoline-3-carboxylic acid 3.7 g (11 mmol) of the above ester were heated under reflux conditions for 1 h in 150 ml of 2N sodium hydroxide solution/ethanol (1:1). The mixture was concentrated in vacuo, the residue was acidified, and the mixture was treated with tetrahydrofuran until the solution became clear and concentrated in vacuo, and 3.0 g of the precipitated product were filtered off with suction; m.p. 139–141° C.

h) N-((1-Chloro-4-hydroxy-7-(2-propyloxy)isoquinolin-3-yl)carbonyl)glycine 1-pentyl ester 4.8 g (17 mmol) of the above isoquinolinecarboxylic acid were treated in 600 ml of dichloromethane with 8.9 ml (70 mmol) of N-ethylmorpholine ("NEM"), 6.3 g (20 mmol) of glycine 1-pentyl ester tosylate, 2.7 g (20 mmol) of 1-hydroxy-1 H-benzotriazole ("HOBT") and 8.5 g (20 mmol) of N-cyclohexyl-N'-(2-morpholinoethyl) carbodiimide methyl-p-toluenesulfonate ("CMC") and the mixture was stirred at 20° C. for 8 days.

It was then concentrated in vacuo, the residue was dissolved in ethyl acetate, and the solution was extracted with aqueous sodium bicarbonate solution. The ethyl acetate phase was shaken with 2N aqueous hydrochloric acid, then with water, dried and concentrated. 3.5 g of product were obtained; m.p. 70–72° C. After treating with petroleum ether; m.p. 73–75° C.

i) N-((1-Chloro-4-hydroxy-7-(2-propyloxy)isoquinolin-3-yl)carbonyl)glycine was obtained as follows:

4.6 g (11 mmol) of the above glycine ester was stirred in 100 ml of 1.5N methanolic sodium hydroxide solution for 1 h, a thick precipitate being formed after 15 min. The mixture was then concentrated in vacuo, the residue was dissolved in water, and the solution was shaken once with diethyl ether, clarified with activated carbon and acidified with aqueous hydrochloric acid with cooling. 3.5 g of the colorless product were obtained; m.p. 207–208° C.

Example 2

N-((1-Chloro-4-hydroxy-6-(2-propyloxy) isoquinolin-3-yl)carbonyl)glycine a) 1-Butyl 1-chloro-4-hydroxy-6-(2-propyloxy) isoquinoline-3-carboxylate 2.0 g of compound B from Example 1e) were reacted with phosphorus oxychloride analogously to 1f). After chromatography using heptane/ethyl acetate (4:1) on silica gel, 1.5 g of product were isolated; m.p. 116–118° C. (from petroleum ether).

b) 1-Chloro-4-hydroxy-6-(2-propyloxy)isoquinoline-3-carboxylic acid 3.3 g of the above ester were hydrolyzed analogously to Example 1g). 2.8 g of product were obtained; m.p. 186–188° C. (from aqueous hydrochloric acid/tetrahydrofuran).

c) N-((1-Chloro-4-hydroxy-6-(2-propyloxy)isoquinolin-3-yl)carbonyl)glycine 1-pentyl ester 2.8 g (10 mmol) of the above carboxylic acid were reacted for 48 hours with 3.2 g (10 mmol) of glycine 1-pentyl estertosylate, 6 ml (40 mmol) of NEM, 1.35 g (10 mmol) of HOBT and 42.4 g (10 mmol) of CMC analogously to Example 1 h). 1.33 g of product were obtained; m.p. 75–77° C. (from petroleum ether).

d) N-((1-Chloro-4-hydroxy-6-(2-propyloxy)isoquinolin-3-yl)carbonyl)glycine was obtained by hydrolyzing 0.45 g of the above glycine ester at 20° C. in a 50 ml of 1.5 N methanolic sodium hydroxide solution. After concentration, the product was crystallized after treating with aqueous hydrochloric acid. 0.37 g of product was obtained; m.p. 223–225° C.

The compounds of Examples 3 to 8 below were obtained by processes analogous to those described in detail in Examples 1 and 2.

Example 3

N-((1-Chloro-4-hydroxy-7-methoxyisoquinolin-3-yl)carbonyl)glycine a) 1-Butyl 4-methoxyphthaloyliminoacetate; m.p. 63–64° C. (from petroleum ether)
b) 1-Butyl 4-hydroxy-7-methoxy-1(2H)-isoquinolone-3-carboxylate; m.p. 125–127° C. (from diethyl ether). Content about 90%.
c) 1-Butyl 1-chloro-4-hydroxy-7-methoxyisoquinoline-3-carboxylate; m.p. 112° C. (from petroleum ether)
d) 1-Chloro-4-hydroxy-7-methoxyisoquinoline-3-carboxylic acid; m.p. 185° C. (from aqueous hydrochloric acid/tetrahydrofuran)
e) N-((1-Chloro-4-hydroxy-7-methoxyisoquinolin-3-yl)carbonyl)glycine 1-pentyl ester; m.p. 93–94° C. (from petroleum ether)
f) N-((1-Chloro-4-hydroxy-7-methoxyisoquinolin-3-yl)carbonyl)glycine was obtained by hydrolysis of the above glycine ester; m.p. 231° C. (from aqueous hydrochloric acid/tetrahydrofuran).

Example 4

N-((1-Chloro-4-hydroxy-6-methoxyisoquinolin-3-yl)carbonyl)glycine a) 1-Butyl 4-hydroxy-6-methoxy-1 (2H)-isoquinolone-3-carboxylate; m.p. 193–195° C. (from aqueous hydrochloric acid/1-butanol
b) 1-Butyl 1-chloro-4-hydroxy-6-methoxyisoquinoline-3-carboxylate; m.p. 114–116° C. (from petroleum ether)
c) 1-Chloro-4-hydroxy-6-methoxyisoquinoline-3-carboxylic acid; m.p. 174–176° C. (from aqueous hydrochloric acid/tetrahydrofuran)
d) N-((1-Chloro-4-hydroxy-6-methoxyisoquinolin-3-yl)carbonyl)glycine 1-pentyl ester; m.p. 109–111° C. (from petroleum ether)
e) N-((1-Chloro-4-hydroxy-6-methoxyisoquinolin-3-yl)carbonyl)glycine was obtained by hydrolysis of the above glycine ester; m.p. 212–214° C. (from aqueous hydrochloric acid/tetrahydrofuran).

Example 5

N-((7-(1-Butyloxy)-1-chloro-4-hydroxyisoquinolin-3-yl)carbonyl)glycine a) 4-((1-Butyloxy)phthalic acid;
b) 4-((1-Butyloxy)phthaloylimino)acetic acid;
c) 1-Butyl 4-((1-butyloxy)phthaloylimino)acetic acid;
d) 1-Butyl 7-(1-butyloxy)-4-hydroxy-1(2H)-isoquinolone-3-carboxylate; m.p. 133–135° C. (from n-heptane/ethyl acetate (3:2));
e) 1-Butyl 7-(1-butyloxy)-1-chloro-4-hydroxyisoquinoline-3-carboxylate;
f) 7-(1-Butyloxy)-1-chloro-4-hydroxyisoquinoline-3-carboxylic acid; m.p. 140–142° C. (from aqueous hydrochloric acid/tetrahydrofuran).
g) 1-Butyl N-((7-(1-butyloxy)-1-chloro-4-hydroxyisoquinolin-3-yl)carbonyl)glycine; m.p. 78–80° C. (from petroleum ether)
h) N-((7-(1-Butyloxy)-1-chloro-4-hydroxyisoquinolin-3-yl)carbonyl)glycine was obtained by hydrolysis of the above glycine ester; m.p. 158–160° C. (from ethyl acetate).

Example 6

N-(-6-(1-Butyloxy-1-chloro-4-hydroxyisoquinolin-3-yl)carbonyl)glycine a) 1-Butyl 6-(1-butyloxy)-4-hydroxy-1(2H)-isoquinolone-3-carboxylate; m.p. 160–162° C. (from n-heptane/ethyl acetate (1:1)
b) 1-Butyl 6-(1-butyloxy)-1-chloro-4-hydroxyisoquinoline-3-carboxylate; m.p. 76–78° C. (from n-heptane/ethyl acetate (1:1))
c) 6-(1-Butyloxy)-1-chloro-4-hydroxyisoquinoline-3-carboxylic acid; m.p. 112–113° C. (from tetrahydrofuran/ethanol)
d) N-((6-(1-Butyloxy)-1-chloro-4-hydroxyisoquinolin-3-yl)carbonyl)glycine benzyl ester;
e) N-(-6-(1-Butyloxy-1-chloro-4-hydroxyisoquinolin-3-yl)carbonyl)glycine; m.p. 182–184° C. (from aqueous hydrochloric acid/tetrahydrofuran).

Example 7

N-((6-Benzyloxy-1-chloro-4-hydroxyisoquinolin-3-yl)carbonyl)glycine a) 1-Butyl 4-benzyloxyphthaloyliminoacetate; m.p. 59–61° C. (from n-heptane/ethyl acetate (1:1))
b) 1-Butyl 6-benzyloxy-4-hydroxy-1(2H)-isoquinolone-3-carboxylate; m.p. 193–195° C. (from butanol/ethyl acetate)
c) 1-Butyl 6-benzyloxy-1-chloro-4-hydroxyisoquinoline-3-carboxylate;
d) 6-Benzyloxy-1-chloro-4-hydroxyisoquinoline-3-carboxylic acid; m.p. 203–205° C. (from aqueous hydrochloric acid/tetrahydrofuran)
e) N-((6-Benzyloxy-1-chloro-4-hydroxyisoquinolin-3-yl)carbonyl)glycine ethyl ester; m.p. 124–127° C. (from diisopropyl ether)
f) N-((6-Benzyloxy-1-chloro-4-hydroxyisoquinolin-3-yl)carbonyl)glycine; m.p. 210–211° C. (from diethyl ether).

Example 8

N-((7-Benzyloxy-1-chloro-4-hydroxyisoquinolin-3-yl)carbonyl)glycine a) 1-Butyl 7-benzyloxy-4-hydroxy-1(2H)-isoquinolone-3-carboxylate;

b) 1-Butyl 7-benzyloxy-1-chloro-4-hydroxyisoquinoline-3-carboxylate; m.p. 115–117° C. (from petroleum ether)

c) 7-Benzyloxy-1-chloro-4-hydroxyisoquinoline-3-carboxylic acid; m.p. 166–168° C. (from aqueous hydrochloric acid/tetrahydrofuran)

d) N-((7-Benzyloxy-1-chloro-4-hydroxyisoquinolin-3-yl)carbonyl)glycine 1-pentyl ester; m.p. 121–123° C. (from diisopropyl ether)

e) N-((7-Benzyloxy-1-chloro-4-hydroxyisoquinolin-3-yl)carbonyl)glycine; m.p. 194–196° C. (from aqueous hydrochloric acid/tetrahydrofuran)

Example 9

N-((1-Chloro-4-hydroxyisoquinolin-3-yl)carbonyl)glycine a) Methyl 1-chloro-4-hydroxyisoquinoline-3-carboxylate 2.84 g (13 mmol) of methyl 4-hydroxy-1 (2H)-isoquinolone-3-carboxylate (prepared as in M. Suzuki, SYNTHESIS, 461 (1978)) was stirred at 70° C. for 3 h in 25 ml of phosphorus oxychloride. After cooling, the mixture was added to 500 ml of ice water, the precipitate was filtered off with suction next morning and dried at 70° C. under an IR Lamp. 2.96 g of product were obtained; m.p. 168° C.

b) 1-Chloro-4-hydroxyisoquinoline-3-carboxylic acid 41.0 g (0.17 mmol) of the above ester were stirred at 90° C. for 5 h in 500 ml of ethanol and 500 ml of 2N aqueous sodium hydroxide solution. After acidifying with aqueous hydrochloric acid to pH 2, 38.9 g of product were obtained; m.p. 192° C. (decomposition).

c) N-((1-Chloro-4-hydroxyisoquinolin-3-yl)carbonyl)glycine methyl ester 1.12 g (5.0 mmol) of the above carboxylic acid and 0.63 g (5.0 mmol) of glycine methyl ester hydrochloride were treated with 0.7 ml of triethylamine, 2.60 g of (benzotriazol-1-yloxy)-tripyrrolidinophosphonium hexafluorophosphate (PyBOP) and 1.7 ml of ethyldiisopropylamine in anhydrous dichloromethane and the mixture was stirred at 20° C. for 3 h. After filtering off undissolved matter, it was washed three times with water, the organic phases dried and concentrated, and the residue was purified using dichloromethane on silica gel. 0.72 g of product was obtained; m.p. 129° C.

d) N-((1-Chloro-4-hydroxyisoquinolin-3-yl)carbonyl)glycine was obtained by stirring 14.1 g (48.1 mmol) of the above ester dissolved in 100 ml of tetrahydrofuran with 100 ml of 1N sodium hydroxide solution for 2 h at 20° C. The mixture was then concentrated in vacuo, diluted with water and extracted three times with dichloromethane, the aqueous phase was brought to pH 3 using conc. hydrochloric acid, and the precipitated product was filtered off with suction and dried. 12.38 g of product were obtained; m.p. 213° C. (decomposition).

Example 10

N-((1,6,7-Trichloro-4-hydroxyisoquinolin-3-yl)carbonyl)glycine (was obtained analogously to Suzuki et al., SYNTHESIS 461 (1978) or Nunami and Suzuki, CHEM. PHARM. BULL. 27 (1979):

a) Methyl 6,7-dichloro-4-hydroxy-1(2H)-isoquinolone-3-carboxylate; m.p. 295° C. (with decomposition, from methanol)

b) Methyl 1,6,7-trichloro-4-hydroxyisoquinoline-3-carboxylate; m.p. 246–248° C. (from water)

c) 1,6,7-Trichloro-4-hydroxyisoquinoline-3-carboxylate; m.p. 200° C. (with decomposition from aqueous hydrochloric acid/tetrahydrofuran)

d) 1-Butyl N-((1,6,7-trichloro-4-hydroxyisoquinolin-3-yl)carbonyl)glycine; m.p. 156–158° C. (from diisopropyl ether)

e) N-((1,6,7-Trichloro-4-hydroxyisoquinolin-3-yl)carbonyl)glycine; m.p. 265° C. (with decomposition from aqueous hydrochloric acid).

Example 11

N-((8-Chloro-4-hydroxyisoquinolin-3-yl)carbonyl)glycine a) 8-Chloro-4-hydroxyisoquinoline-3-carboxylic acid; m.p. 209° C. (from aqueous hydrochloric acid)

b) N-((8-Chloro-4-hydroxyisoquinolin-3-yl)carbonyl)glycine methyl ester; m.p. 103° C. (from ethyl acetate/n-heptane (1:1))

c) N-((8-Chloro-4-hydroxyisoquinolin-3-yl)carbonyl)glycine; m.p. 232° C. (from water).

Example 12

N-((4-Hydroxy-8-methoxyisoquinolin-3-yl)carbonyl)glycine a) 4-Hydroxy-8-methoxyisoquinoline-3-carboxylic acid; m.p. 217° C. (from aqueous hydrochloric acid)

b) N-((4-Hydroxy-8-methoxyisoquinolin-3-yl)carbonyl)glycine; m.p. 168° C. (from water).

Example 13

N-((7-(1-Butyloxy)-4-hydroxyisoquinolin-3-yl)carbonyl)glycine a) 1-Butyl 7-(1-butyloxy)-4-hydroxyisoquinolin-3-yl)carboxylate The compound from Example 5e) was first hydrogenated in tetrahydrofuran using Pd and hydrogen. Complete reaction takes place in methanol plus 5% formic acid using Pd/C; oily crude product.

b) 7-(1-Butyloxy)-4-hydroxyisoquinoline-3-carboxylic acid; m.p. 180° C. (with decomposition, from aqueous hydrochloric acid/tetrahydrofuran)

c) 1-Butyl N-((7-(1-butyloxy)-4-hydroxyisoquinolin-3-yl)carbonyl)glycine oily crude product d) N-((7-(1-Butyloxy)-4-hydroxyisoquinolin-3-yl)carbonyl)glycine; m.p. 151–153° C. (from aqueous hydrochloric acid).

Example 14

N-((6-(1-Butyloxy)-4-hydroxyisoquinolin-3-yl)carbonyl)glycine a) 1-Butyl 6-(1-butyloxy)-4-hydroxyisoquinoline-3-carboxylate was obtained by hydrogenation of the compound from Example 6b); oily crude product.

b) 6-(1-Butyloxy)-4-hydroxyisoquinoline-3-carboxylic acid; m.p. 185–187° C. (from aqueous hydrochloric acid/tetrahydrofuran)

c) N-((6-(1-Butyloxy)-4-hydroxyisoquinolin-3-yl)carbonyl)glycine benzyl ester' m.p. 98–100° C. (from N-heptane/ethyl acetate(1:1))

d) N-((6-(1-Butyloxy)-4-hydroxyisoquinolin-3-yl)carbonyl)glycine was obtained by hydrogenation of the above benzyl ester; m.p. 199–200° C. (from petroleum ether).

Example 15

N-((4-Hydroxy-7-(2-propyloxy)isoquinolin-3-yl)carbonyl)glycine

The compounds of Examples 16 to 18 can be obtained by a process analogous to that disclosed with respect to the compound of Example 1.

Example 16

N-((4-Hydroxy-7-(3-pentyloxy)isoquinolin-3-yl)carbonyl)glycine

Example 17

N-((4-Hydroxy-7-trifluoromethoxyisoquinolin-3-yl)carbonyl)glycine

Example 18

N-((7-Difluoromethoxy-4-hydroxyisoquinolin-3-yl)carbonyl)glycine

Example 19

1-Chloro-4-hydroxy-7-(2-propyloxy)isoquinoline-3-carboxylic acid N-(2-hydroxyethyl)amide 0.3 g of the compound from Example 1f was stirred at 85° C. for 1 h in 5 ml of 2-aminoethanol, the mixture was then treated with 30 ml of water, adjusted to pH 1 with cooling using half-concentrated, aqueous hydrochloric acid and extracted twice with ethyl acetate, the extract was dried and concentrated and the residue was crystallized using a little diisopropyl ether/petroleum ether (1:1). 0.21 g of 1-Chloro-4-hydroxy-7-(2-propyloxy)isoquinoline-3-carboxylic acid N-(2-hydroxyethyl)amide was obtained; m.p. 102–104° C.

Example 20

1-Chloro-4-hydroxy-6-(2-propyloxy)isoquinoline-3-carboxylic acid N-(2-hydroxyethyl)amide 1-Chloro-4-hydroxy-6-(2-propyloxy)isoquinoline-3-carboxylic acid N-(2-hydroxyethyl)amide was prepared analogously to Example 19 starting from the compound of Example 2a) and 2-aminoethanol; m.p. 155–156° C. (from petroleum ether).

Example 21

1-Chloro-4-hydroxy-7-methoxyisoquinoline-3-carboxylic acid N-(2-hydroxyethyl)amide was prepared analogously to Example 19 starting from the compound of Example 3c) and 2-aminoethanol; m.p. 165–167° C. (from diisopropyl ether).

Example 22

1-Chloro-4-hydroxy-6-methoxyisoquinoline-3-carboxylic acid N-(2-hydroxyethyl)amide was prepared analogously to Example 19 starting from the compound of Example 4a) and 2-aminoethanol; m.p. 117–119° C. (from diisopropyl ether).

Example 23

7-(1-Butyloxy)-1-chloro-4-hydroxyisoquinoline-3-carboxylic acid N-(2-hydroxyethyl)amide was prepared analogously to Example 19 starting from the compound of Example 5e) and 2-aminoethanol; m.p. 118–120° C. (from diisopropyl ether).

The foregoing written description relates to various embodiments of the present invention, and is not intended to impose any limits on the scope of the invention or its equivalents. Numerous changes and modifications may be made therein without departing from the spirit and scope of the invention as defined in the following claims.

What is claimed is:

1. A compound of the formula I, or a physiologically active salt thereof:

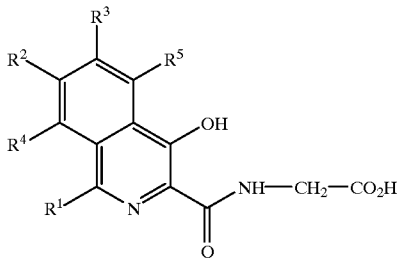

in which

R$^1$ is hydrogen or chlorine;

R$^2$ is hydrogen, (C$_1$–C$_8$)-alkyl, (C$_1$–C$_8$)-alkoxy, chlorine, trifluoromethyl, hydroxyl, benzyloxy, which is unsubstituted or substituted by a substituent selected from the group consisting of (C$_1$–C$_5$)-alkyl and (C$_1$–C$_5$)-alkoxy, or fluoroalkoxy of the formula

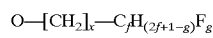

where x=0 or 1, f=an integer from 1 to 5, and g=an integer from 1 to (2f+1);

R$^3$ is hydrogen, (C$_1$–C$_8$)-alkyl, (C$_1$–C$_8$)-alkoxy, fluorine, chlorine, cyano, trifluoromethyl, hydroxyl, benzyloxy which is unsubstituted or substituted by a substituent selected from the group consisting of (C$_1$–C$_5$)-alkyl and (C$_1$–C$_5$)-alkoxy, or fluoroalkoxy of the formula

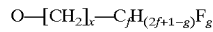

in which x, f, and g are as defined above; and

R$^4$ and R$^5$ independently are hydrogen, (C$_1$–C$_5$)-alkyl, fluorine, chlorine, bromine, trifluoromethyl, cyano, (C$_1$–C$_5$)-alkoxy, or fluoroalkoxy of the formula

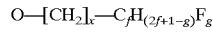

in which x, f, and g are as defined above, with the proviso that R$^1$, R$^2$, R$^3$, R$^4$, and R$^5$ are not all simultaneously hydrogen.

2. A compound of the formula I as claimed in claim 1, or a physiologically active salt thereof, in which R$^1$ is hydrogen or chlorine;

R$^2$ is hydrogen, (C$_1$–C$_8$)-alkyl, (C$_1$–C$_8$)-alkoxy, chlorine, trifluoromethyl, hydroxyl, benzyloxy, or fluoroalkoxy of the formula

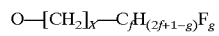

where x=0 or 1, f=an integer from 1 to 5, and g=an integer from 1 to (2f+1);

R$^3$ is hydrogen, (C$_1$–C$_8$)-alkyl, (C$_1$–C$_8$)-alkoxy, fluorine, chlorine, cyano, trifluoromethyl, hydroxyl, benzyloxy, or fluoroalkoxy of the formula

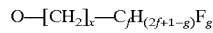

in which x, f, and g are as defined above,

R⁴ is hydrogen, (C₁–C₈)-alkoxy, fluorine, chlorine, trifluoromethyl, cyano, or fluoroalkoxy of the formula

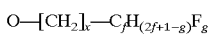

in which x, f, and g are as defined above; and

R⁵ is hydrogen.

3. A compound of the formula I as claimed in claim 1, or a physiologically active salt thereof, in which R¹ is hydrogen or chlorine;

R² is hydrogen, (C₁–C₅)-alkoxy, chlorine, benzyloxy, or fluoroalkoxy where x=0, and f=1;

R³ is hydrogen, (C₁–C₅)-alkoxy, chlorine or benzyloxy;

R⁴ is hydrogen, chlorine or methoxy; and

R⁵ is hydrogen.

4. A compound of the formula I as claimed in claim 1, or a physiologically active salt thereof, in which R¹ is hydrogen or chlorine;

R² is hydrogen, (C₁–C₈)-alkoxy, chlorine, hydroxyl or benzyloxy;

R³ is hydrogen, (C₁–C₈)-alkoxy, fluorine, chlorine, hydroxyl or benzyloxy;

R⁴ is hydrogen or chlorine; and

R⁵ is hydrogen.

5. A compound of the formula I as claimed in claim 1, or a physiologically active salt thereof, in which R¹ is hydrogen or chlorine;

R² is (C₁–C₈)-alkoxy, chlorine, or benzyloxy; and

R³, R⁴ and R⁵ are hydrogen.

6. A compound of the formula I as claimed in claim 1, or a physiologically active salt thereof, in which R¹ is hydrogen or chlorine;

R² is hydrogen or chlorine;

R³ is (C₁–C₈)-alkoxy, chlorine or benzyloxy; and

R⁴ and R⁵ are hydrogen.

7. A compound of the formula I as claimed in claim 1, or a physiologically active salt thereof, in which R¹ is hydrogen or chlorine;

R² and R³ independently are hydrogen or chlorine;

R⁴ is (C₁–C₆)-alkoxy, chlorine, or benzyloxy; and

R⁵ is hydrogen.

8. A compound of the formula I as claimed in claim 1, or a physiologically physically active salt thereof, in which R¹ is hydrogen or chlorine;

R² is (C₁–C₆)-alkoxy or benzyloxy; and

R³, R⁴ and R⁵ are hydrogen.

9. A compound of the formula I as claimed in claim 1, or a physiologically active salt thereof, in which R¹ is hydrogen or chlorine;

R² is hydrogen;

R³ is (C₁–C₆)-alkoxy or benzyloxy; and

R⁴ and R⁵ are hydrogen.

10. A compound of the formula I as claimed in claim 1, or a physiologically active salt thereof, in which R¹ is hydrogen or chlorine;

R² is (C₁–C₆)-alkoxy; and

R³, R⁴ and R⁵ are hydrogen.

11. A compound of the formula I as claimed in claim 1, or a physiologically active salt thereof, in which R¹ is hydrogen or chlorine;

R² is hydrogen;

R³ is (C₁–C₆)-alkoxy; and

R⁴ and R⁵ are hydrogen.

12. A compound of the formula I as claimed in claim 1, wherein the compound is

N-((1-Chloro-4-hydroxyisoquinolin-3-yl)carbonyl)glycine;

N-((8-chloro-4-hydroxyisoquinolin-3-yl)carbonyl)glycine;

N-((1-chloro-4-hydroxy-7-(2-propyloxy)isoquinolin-3-yl)carbonyl)glycine; or

N-((4-hydroxy-7-(2-propyloxy)isoquinolin-3yl)carbonyl)glycine.

13. A compound of the formula Ia, or a physiologically active salt thereof:

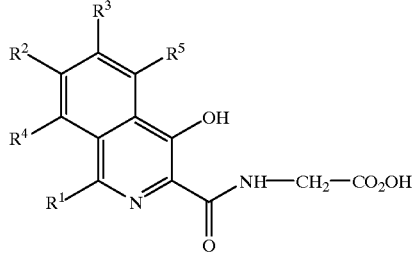

(Ia)

in which

R¹ is hydrogen or chlorine;

R² is hydrogen, (C₁–C₈)-alkyl, (C₁–C₈)-alkoxy, chlorine, trifluoromethyl, hydroxyl, benzyloxy, which is unsubstituted or substituted by a substituent selected from the group consisting of (C₁–C₅)-alkyl, and (C₁–C₅)-alkoxy, or fluoroalkoxy of the formula

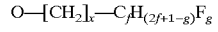

where x=0 or 1, f=an integer from 1 to 5, and g=an integer from 1 to (2f+1);

R³ is hydrogen, (C₁–C₈)-alkyl, (C₁–C₈)-alkoxy, fluorine, chlorine, cyano, trifluoromethyl, hydroxyl, benzyloxy which is unsubstituted or substituted by a substituent selected from the group consisting of (C₁–C₅)-alkyl and (C₁–C₅)-alkoxy, or fluoroalkoxy of the formula

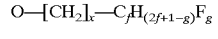

in which x, f, and g are as defined above; and

R⁴ and R⁵ independently are hydrogen, (C₁–C₅)-alkyl, fluorine, chlorine, bromine, trifluoromethyl, cyano, (C₁–C₅)-alkoxy, or fluoroalkoxy of the formula

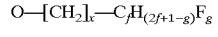

in which x, f, and g are as defined above.

14. A compound of the formula Ia as claimed in claim 13, or a physiologically active salt thereof, in which R¹ is chlorine;

R² and R³ independently are hydrogen or (C₁–C₄)-alkoxy; and

R⁴ and R⁵ are hydrogen.

15. A compound of the formula Ia as claimed in claim 13, or a physiologically active salt thereof, in which
- $R^1$ is hydrogen or chlorine;
- $R^2$ is $(C_1-C_6)$-alkoxy; and
- $R^3$, $R^4$ and $R^5$ are hydrogen.

16. A compound of the formula Ia as claimed in claim 13, or a physiologically active salt thereof, in which
- $R^1$ is hydrogen or chlorine;
- $R^2$ is hydrogen;
- $R^3$ is $(C_1-C_6)$-alkoxy; and
- $R^4$ and $R^5$ are hydrogen.

17. A compound of the formula Ia as claimed in claim 13, wherein the compound is
1-Chloro-4-hydroxy-7-(2-propyloxy)isoquinoline-3-carboxylic acid N-(2-hydroxyethyl)amide.

18. A composition comprising a prodrug, or a physiologically active salt thereof, of a compound of claim 1.

19. A process for the preparation of a compound of the formula I:

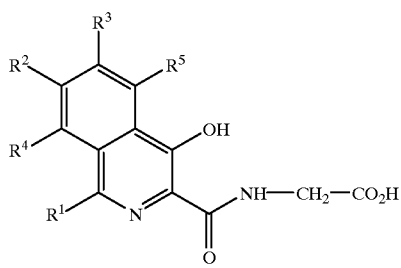

in which
- $R^1$ is hydrogen or chlorine:
- $R^2$ is hydrogen, $(C_1-C_8)$-alkyl, $(C_1-C_8)$-alkoxy, chlorine, trifluoromethyl, hydroxyl, benzyloxy which is unsubstituted or substituted by a substituent selected from the group consisting of $(C_1-C_5)$-alkyl and $(C_1-C_5)$-alkoxy, or fluoroalkoxy of the formula

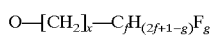

where
x=0 or 1,
f=an integer from 1 to 5, and
g=an integer from 1 to (2f+1);

- $R^3$ is hydrogen, $(C_1-C_8)$-alkyl, $(C_1-C_8)$-alkoxy, fluorine, chlorine, cyano, trifluoromethyl, hydroxyl, benzyloxy which is unsubstituted or substituted by a substituent selected from the group consisting of $(C_1-C_5)$-alkyl and $(C_1-C_5)$-alkoxy, or fluoroalkoxy of the formula

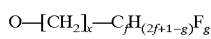

in which x, f, and g are as defined above; and

- $R^4$ and $R^5$ independently are hydrogen, $(C_1-C_5)$-alkyl, fluorine, chlorine, bromine, trifluoromethyl, cyano, $(C_1-C_5)$-alkoxy, or fluoroalkoxy of the formula

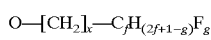

in which x, f, and g are as defined above;
which comprises
I.i) reacting a quinoline-2-carboxylic acid of the formula II

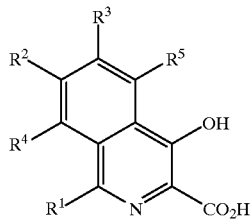

with an amino ester of the formula III:

in which R is H, $(C_1-C_8)$-alkyl, or benzyl;
to give an amide ester of the formula IV:

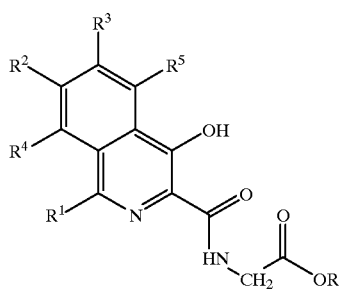

and
I.ii) releasing the compound of the formula I:

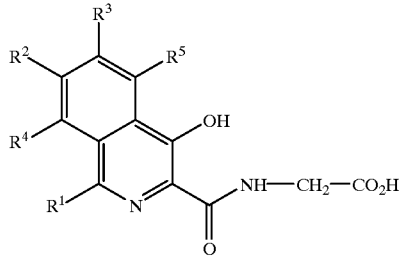

from its ester of the formula IV.

20. A process for the preparation of a compound of the formula Ia as claimed in claim 13, comprising the step of reacting a compound of the formula IIa:

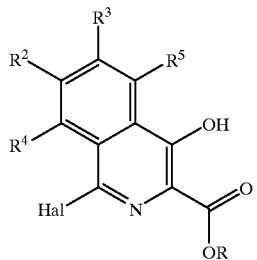

in which R is H, $(C_1-C_8)$-alkyl, or benzyl; with 2-aminoethanol.

21. A method for the inhibition of collagen biosynthesis, comprising the step of administering to a host in need of such inhibition an effective amount of a compound of claim 1.

22. A method for the inhibition of collagen biosynthesis, comprising the step of administering to a host in need of such inhibition an effective amount of a prodrug, or a physiologically active salt thereof, of a compound of claim 1.

23. A method for the inhibition of collagen biosynthesis, comprising the step of administering to a host in need of such inhibition an effective amount of a compound of claim 13.

24. The method as claimed in claim 23, wherein the collagen biosynthesis is collagen biosynthesis in the liver.

25. A method for the inhibition of prolyl-4-hydroxylase, comprising the step of administering to a host in need of such inhibition an effective amount of a compound of claim 1.

26. A method for the inhibition of prolyl-4-hydroxylase, comprising the step of administering to a host in need of such inhibition an effective amount of a prodrug, or a physiologically active salt thereof, of a compound of claim 1.

27. A method for the inhibition of prolyl-4-hydroxylase, comprising the step of administering to a host in need of such inhibition an effective amount of a compound of claim 13.

28. A method for the suppression of a fibrotic disorder, comprising the step of administering to a host in need of such suppression an effective amount of a compound of claim 1.

29. A method for the suppression of a fibrotic disorder, comprising the step of administering to a host in need of such suppression an effective amount of a prodrug, or a physiologically active salt thereof, of a compound of claim 1.

30. A method for the suppression of a fibrotic disorder, comprising the step of administering to a host in need of such suppression an effective amount of a compound of claim 13.

31. A method for the treatment of a fibrotic disorder, comprising the step of administering to a host in need of such treatment an effective amount of a compound of claim 1.

32. The method as claimed in claim 31, wherein the fibrotic disorder is a disorder of the liver, kidney, lung, or skin.

33. A method for the treatment of a fibrotic disorder, comprising the step of administering to a host in need of such treatment an effective amount of a compound of claim 13.

34. The method as claimed in claim 33, wherein the fibrotic disorder is a disorder of the liver, kidney, lung, or skin.

35. The method as claimed in claim 34, wherein the fibrotic disorder is a disorder of the liver.

36. A pharmaceutical composition comprising a compound of claim 1, together with a pharmaceutically tolerable excipient.

37. A pharmaceutical composition comprising a compound of claim 13, together with a pharmaceutically tolerable excipient.

* * * * *

UNITED STATES PATENT AND TRADEMARK OFFICE
CERTIFICATE OF CORRECTION

PATENT NO.: 6,093,730

DATED: July 25, 2000

INVENTORS: Klaus WEIDMANN et al.

It is certified that an error appears in the above-identified patent and that said Letters Patent is hereby corrected as shown below:

Column 4, lines 30-40, in formula (Ia), "$CO_2OH$" should read --$CH_2OH$--.

Claim 13, Column 22, In Formula (Ia), "$CO_2OH$" should read --$CH_2OH$;--.

Claim 19, Column 23, line 36, "chlorine:" should read --chlorine;--.

Signed and Sealed this

Twenty-fourth Day of April, 2001

*Attest:*

NICHOLAS P. GODICI

*Attesting Officer*  *Acting Director of the United States Patent and Trademark Office*